United States Patent
Chasen

(10) Patent No.: US 6,610,121 B2
(45) Date of Patent: Aug. 26, 2003

(54) ODOR REMOVAL SYSTEM

(75) Inventor: James E. Chasen, West Haven, CT (US)

(73) Assignee: HP Intellectual Corp., Wilmington, DE (US)

( * ) Notice: Subject to any disclaimer, the term of this patent is extended or adjusted under 35 U.S.C. 154(b) by 3 days.

(21) Appl. No.: 10/098,960

(22) Filed: Mar. 13, 2002

(65) Prior Publication Data

US 2003/0126987 A1 Jul. 10, 2003

Related U.S. Application Data

(63) Continuation-in-part of application No. 10/045,932, filed on Jan. 9, 2002.

(51) Int. Cl.[7] .................................................. B01F 3/04
(52) U.S. Cl. ................................ 95/1; 96/222; 96/397; 55/486; 261/115; 261/DIG. 65; 261/DIG. 88; 4/217
(58) Field of Search ..................... 95/1; 96/222, 397; 55/482, 486; 261/115, 107, DIG. 65, DIG. 88; 4/213, 217, 228.1

(56) References Cited

U.S. PATENT DOCUMENTS

| | | | |
|---|---|---|---|
| 2,860,725 A | 11/1958 | Cawl et al. | |
| 2,911,062 A | 11/1959 | Ferraria | |
| 3,745,965 A | 7/1973 | Ljung et al. | 116/112 |
| 4,001,912 A | 1/1977 | Eriksson | 15/339 |
| 4,184,225 A | 1/1980 | Leinfelt | 15/339 |
| 5,192,424 A | 3/1993 | Beyne et al. | 210/85 |
| 5,294,407 A | 3/1994 | Succi et al. | 422/119 |
| 5,378,254 A | 1/1995 | Maly et al. | 55/271 |
| 5,413,097 A | 5/1995 | Birenheide et al. | 128/206.17 |
| 5,454,122 A * | 10/1995 | Bergeron | 4/217 |
| 5,674,381 A | 10/1997 | Den Dekker | 210/85 |
| 5,772,732 A | 6/1998 | James et al. | 95/25 |
| 5,810,908 A | 9/1998 | Gray et al. | 95/25 |
| 5,907,886 A | 6/1999 | Buscher | 15/319 |
| 5,914,453 A | 6/1999 | James et al. | 95/14 |
| 5,920,043 A | 7/1999 | Wang et al. | 200/52 R |
| 6,051,144 A | 4/2000 | Clack et al. | 210/739 |
| 6,073,302 A | 6/2000 | Buscher | 15/339 |
| 6,077,336 A | 6/2000 | Ulrich et al. | 96/222 |
| 6,106,705 A | 8/2000 | Giordano et al. | 210/87 |
| 6,126,729 A * | 10/2000 | Smith | 96/222 |
| 6,186,140 B1 | 2/2001 | Hoague | 128/202.22 |
| 6,214,239 B1 | 4/2001 | Renau | 210/739 |
| 6,217,641 B1 | 4/2001 | Gunnarsson | 96/404 |
| 6,233,750 B1 * | 5/2001 | Donald et al. | 4/213 |

FOREIGN PATENT DOCUMENTS

GB 2141816 A * 1/1985

* cited by examiner

Primary Examiner—Robert Hopkins
(74) Attorney, Agent, or Firm—Barry E. Deutsch

(57) ABSTRACT

An air filter assembly including a frame, a filter and an odor eliminator liquid. The frame forms an air flow channel. The filter is connected to the frame in the air flow channel. The filter includes at least one filter element. The odor eliminator liquid is located on a first one of the filter elements.

22 Claims, 5 Drawing Sheets

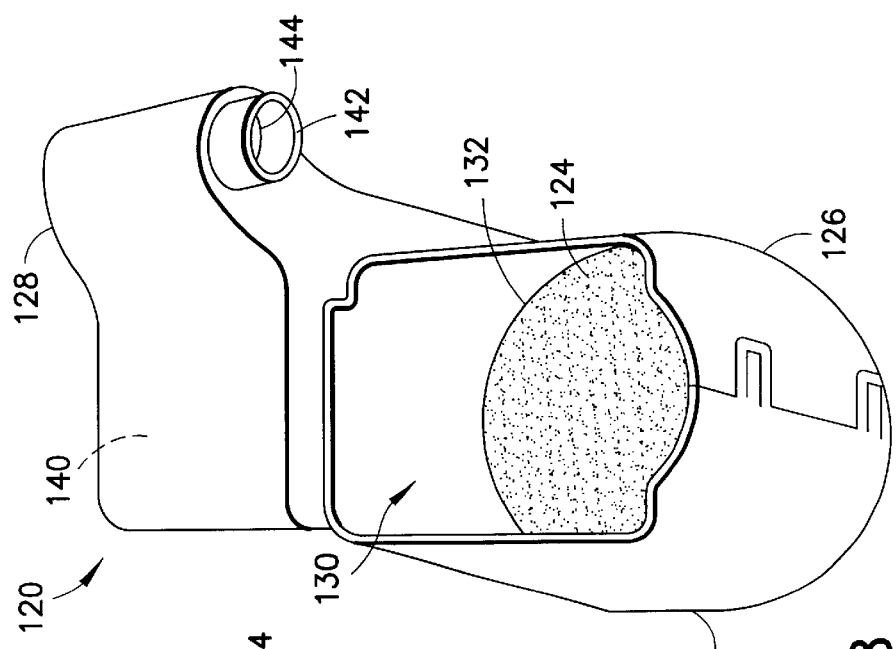
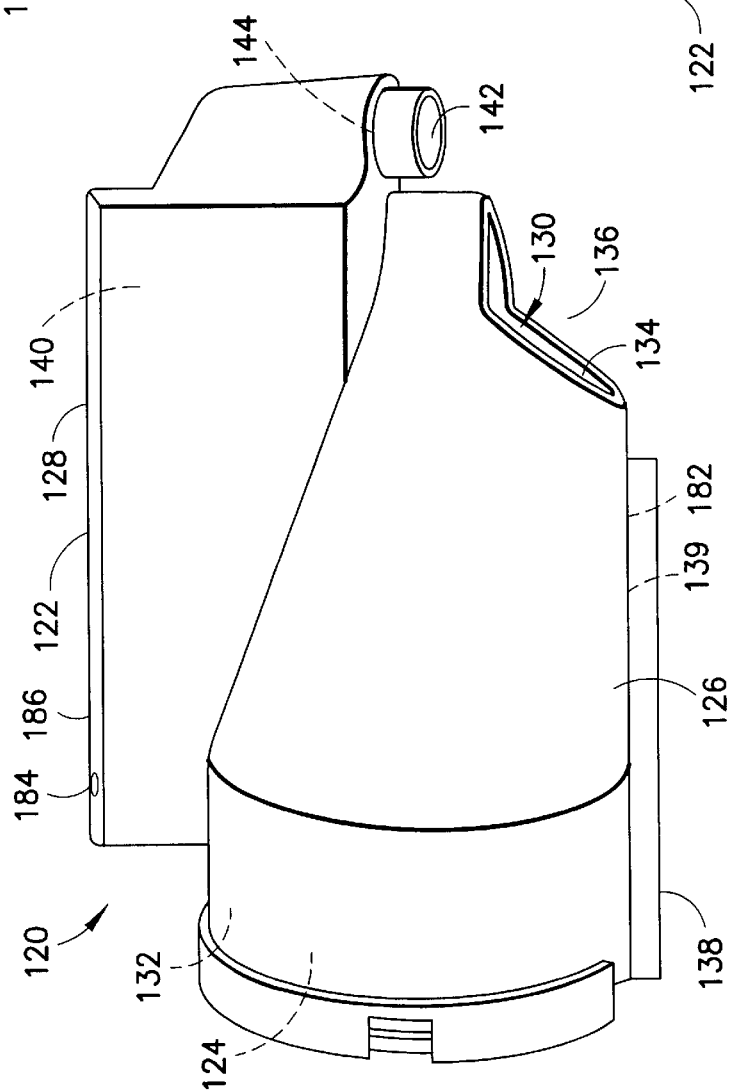
FIG.8
FIG.7

ODOR REMOVAL SYSTEM

CROSS-REFERENCE TO RELATED APPLICATION

This application is a continuation-in-part of copending application(s) application Ser. No. 10/045,932 filed on Jan. 9, 2002.

BACKGROUND OF THE INVENTION

1. Field of the Invention

The present invention relates to air filtration and, more particularly, to a method and apparatus which comprises an air filter element and an odor eliminator liquid which is sprayed onto the air filter element.

2. Brief Description of Prior Developments

Elimination of odors from bathrooms or toilet facilities has been a continuing problem. One solution has been to exhaust odors through walls or floors to outside the bathroom. However, this type of solution is relatively expensive and labor intensive. Holes must be drilled in walls or floors. Thus, it is not easy to do for an average homeowner. Another solution has been the removal of odors from the bathroom area via a ceiling vent fan. Installation of a ceiling vent fan and exhaust conduit can also be expensive and labor intensive. In addition, the bathroom user smells the odors before they reach the exhaust fan. Another solution has included piping of toilet odors through a carbon filter before being exhausted from the bathroom. This has limited effectiveness in removing odors. Another solution has been the use of perfumes or sprays to cover-up the odors. However, perfumes or cover-up spells do not remove the odors. The smells just mask the odors. Other solutions have included drop-ins which are inserted into a toilet, candles or other burning objects inside the bathroom, and leaving a bathroom window open. However, all of these prior solutions have their own disadvantages.

There is a desire to provide a new type of toilet odor removal system which can remove odors relatively effectively. There is a desire for a toilet odor removal system which is relatively easy to install by an average consumer without special tools or equipment. There is a desire for a toilet odor removal system which can neutralize and eliminate odors very effectively before the air is exhausted into or out of the bathroom.

SUMMARY OF THE INVENTION

In accordance with one aspect of the present invention, an air deodorizer cartridge is provided comprising a frame and at least one air filter element. The frame includes a first section and a second section. The first section forms an air flow channel and an air filter holding area. The second section forms a liquid reservoir. The air filter element is located in the filter holding area. The first and second sections of the frame are fixedly directly coupled to each other as a unitary structure for insertion of the air deodorizer cartridge into an air deodorizing apparatus as a singular cartridge unit.

In accordance with another aspect of the present invention, an air deodorizer cartridge is provided comprising a frame, at least one air filter element, and a magnet. The frame forms an air flow channel and an air filter holding area. The air filter element is located in the filter holding area. The magnet is connected to the frame. The frame is sized and shaped to be inserted into a mating receiving area of an air deodorizing apparatus such that the air flow channel mates with a mating air flow channel in the apparatus. The magnet is located on the frame such that, when the cartridge is inserted into the apparatus, the magnet is positioned directly opposite a reed switch of the air deodorizing apparatus to thereby actuate the reed switch.

In accordance with one method of the present invention, a method of manufacturing an air deodorizer cartridge is provided comprising steps of forming a unitary frame with a first section having an air flow channel and a second section having a liquid reservoir; inserting an air filter element into the first section of the frame; and inserting deodorizing liquid into the liquid reservoir of the second section.

BRIEF DESCRIPTION OF THE DRAWINGS

The foregoing aspects and other features of the present invention are explained in the following description, taken in connection with the accompanying drawings, wherein:

FIG. 7 is a side perspective view of one embodiment of an air deodorizer cartridge incorporating features of the present invention;

FIG. 8 is a perspective bottom and rear side view of the air deodorizer cartridge shown in FIG. 7;

DETAILED DESCRIPTION OF THE PREFERRED EMBODIMENTS

Figure 1:
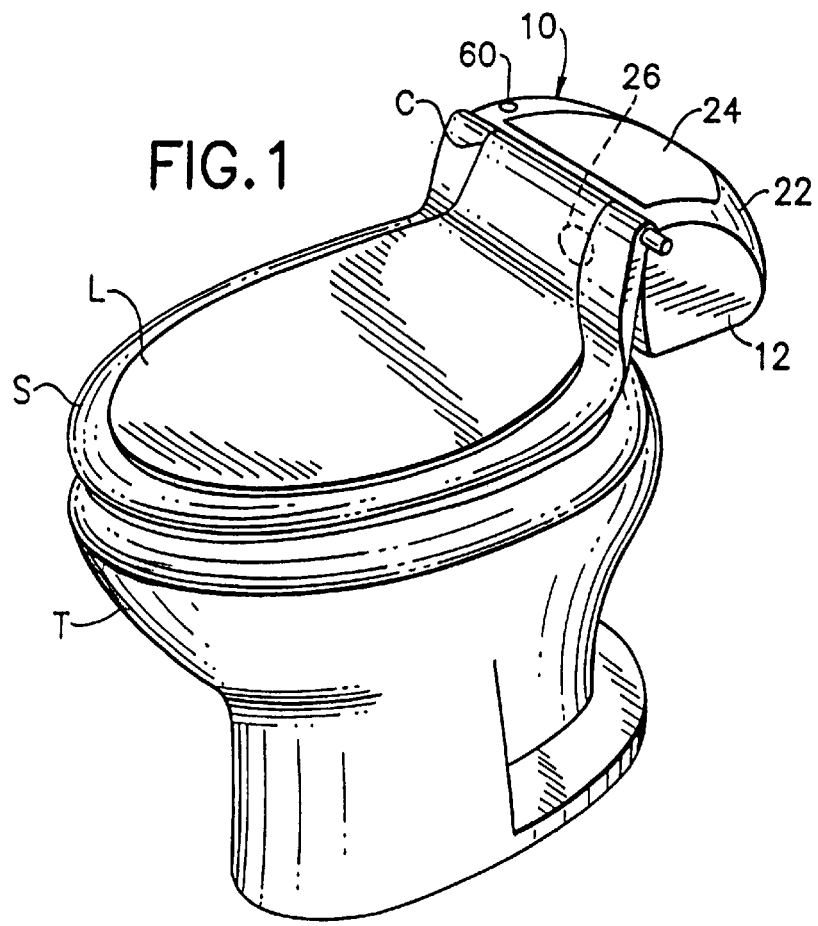
FIG. 1 is a perspective view of a toilet having a system for deodorizing air incorporating features of the present invention.

Referring to FIG. 1, there is shown a perspective view of a toilet bowl T having a deodorizing air system 10 incorporating features of the present invention. Although the present invention will be described with reference to the embodiments shown in the drawings, it should be understood that the present invention can be embodied in many alternate forms of embodiments. In addition, any suitable size, shape or type of elements or materials could be used.

Figure 2:
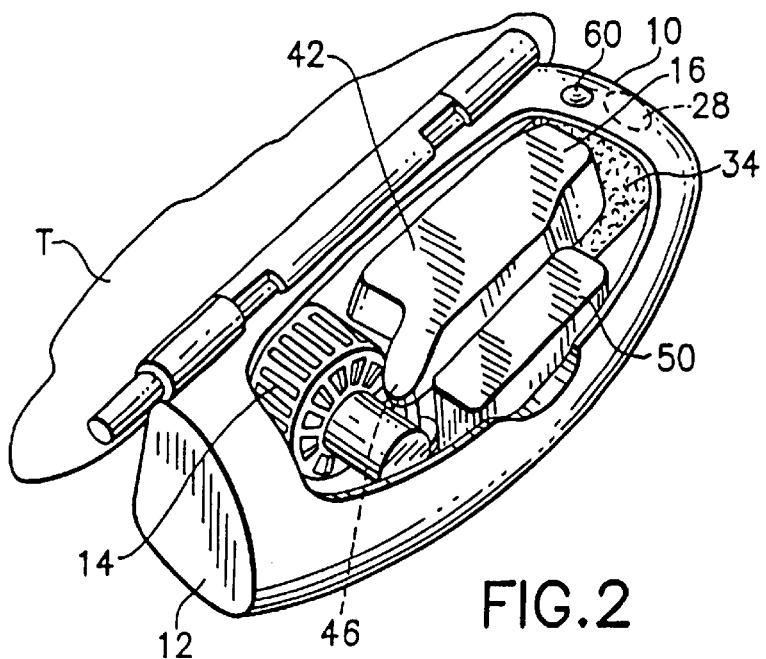
FIG. 2 is a perspective view of the deodorizing air system shown in FIG. 1 having its cover removed.
Figure 3:
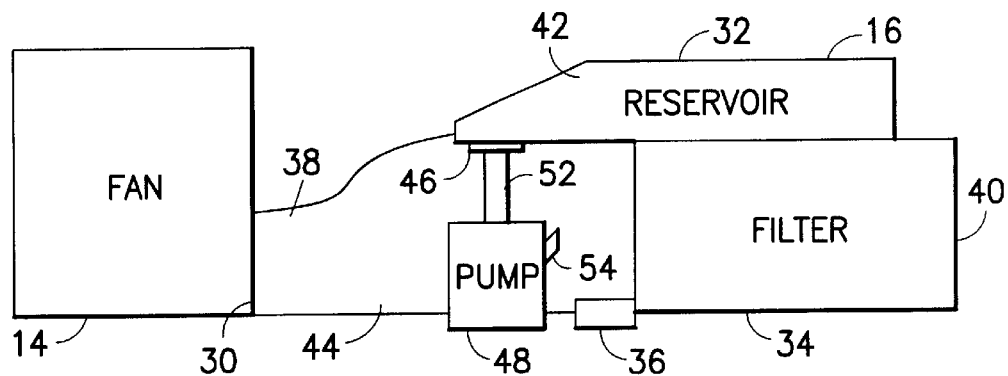
FIG. 3 is a block diagram of components of the deodorizing air system shown in FIG. 2.
Figure 4:
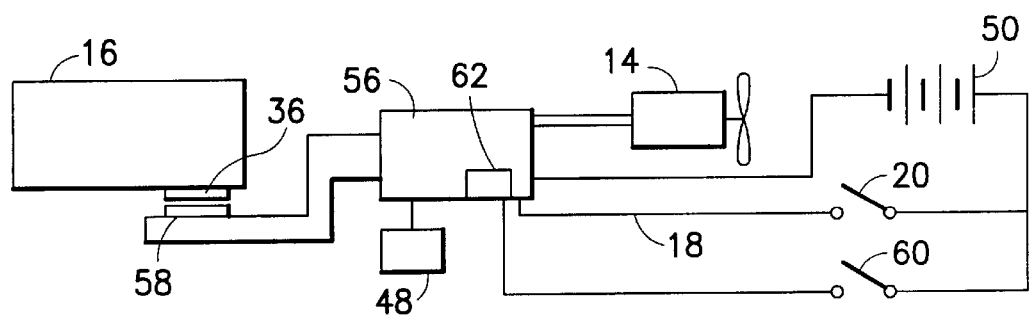
FIG. 4 is a schematic circuit diagram of components used in the deodorizing air system shown in FIG. 2.

Referring also to FIGS. 2–4, the deodorizing air system 10 generally comprises a housing 12, a fan 14, a removable combined air filter and liquid deodorizer cartridge 16, and an electrical circuit 18. In alternate embodiments, additional or alternative components could be provided. The housing 12 is preferably adapted to be mounted to the toilet bowl T at the back end of the toilet proximate the pivotal connection C of the toilet seat S and lid L. However, in an alternative embodiment, the housing 12 could be adapted to be mounted to any suitable location, such as the side or front. In a preferred embodiment, the seat S is biased in a slightly upward position relative to the toilet bowl T, such as by a spring. In this preferred embodiment, the electrical circuit 18 comprises a switch 20 which is adapted to be actuated when a person sits on the seat S. When a person sits on the seat S, the seat S is adapted to pivot downward against the toilet bowl T and close the switch. However, in an alternative embodiment, the switch 20 could be activated by any suitable system, such as an infra red or optical user presence device.

The housing 12 comprises a main housing section 22 and a movable or removable lid 24. The main housing section 22 comprises an air entrance 26 at its bottom, front side. The air entrance 26 communicates with air from inside the toilet bowl T at a gap between the toilet bowl T and the mounting of the seat S and lid L at the connection C. The air inlet can comprise a preliminary filter (not shown) for filtering paper particles which may fly off of toilet paper. The main housing section 22 also comprises an air outlet 28 at a lateral side. In alternate embodiments, the housing 12 could comprise any suitable shape or type of components. The outlet could be at any suitable side or connected to an exhaust pipe.

The fan 14 generally comprises an electric fan with a front facing inlet and a lateral side facing outlet 30. The housing 12 can form an air conduit from the air entrance 26, through the preliminary filter, and to the front facing inlet of the fan 14. The fan 14 includes a centrifugal rotating fan member. However, in alternative embodiments, any suitable fan member(s) could be provided, such as an axial fan member. In the embodiment shown, the fan 14 is a battery operated fan. However, in alternate embodiments, the fan 14 might not be battery operated, such as when the deodorizing air system 10 is connected to a main power supply or is manually actuated. In addition, the inlet and outlet of the fan could be located at any suitable sides of the fan, such as when the fan is connected to suitable air duct conduits.

The cartridge 16 generally comprises a frame 32, a filter 34, and a switch actuator 36. The cartridge 16 is adapted to be removably connected to the outlet 30 from the fan 14 inside the housing 12. The frame 32 generally comprises an air inlet 38, an air outlet 40, a liquid reservoir 42, and a chamber 44. The air inlet 38 is removably connected to the outlet 30. The filter 34 is located at the opposite end of the air inlet 38, proximate the air outlet 40. The chamber 44 forms an open area between the inlet 38 and the filter 34. The liquid reservoir 42 comprises an outlet 46. The liquid reservoir 42 is adapted to hold a supply of deodorizing liquid therein.

The filter 34 is preferably a two-stage filter. However, in alternate embodiments, the filter could comprise more or less than two stages. In a preferred embodiment, the filter 34 comprises a first stage with a first filter element and a second stage with a different second filter element. In one type of embodiment the first filter element comprises a polymer mesh filter and the second filter element comprises activated carbon or zeolite. However, in alternate embodiments, the different stages of the filter element 34 could comprise any suitable type of materials. In alternate embodiments, any suitable type of filter element(s) could be provided. The outlet from the second stage is located proximate the outlet 28 through the housing 12.

The chamber 44 is located between the inlet 38 and the filter 34. The chamber 44 forms an area for air from the fan 14 to pass through and then into the filter 34. The chamber 44 also forms an area for entry of liquid from the reservoir 42 into the air stream between the inlet 38 and the filter 34.

The switch actuator 36 is fixedly attached to the frame 32 of the cartridge 16. In the embodiment shown, the switch actuator 36 comprises a permanent magnet. However, in alternate embodiments, the switch actuator 36 could comprise any suitable type of component. For example, in one alternate embodiment, the switch actuator 36 could comprise electrically conductive material used as an electrical contact. In another alternate embodiment, the switch actuator 36 could comprise a mechanical type of actuator for actuating an electromechanical switch.

The deodorizing air system 10, in the embodiment shown, further comprises a liquid pump 48 and a battery 50. In an alternate embodiment, the liquid pump 48 could be replaced by a vacuum supply device or any other suitable type of liquid movement system for moving liquid from the reservoir 42 into the chamber 44. The liquid pump 48 is preferably battery operated. However, in alternate embodiments, the liquid pump could be actuated by any suitable type of drive system. For example, in one alternate embodiment, the pump 48 could be actuated by movement of the seat S. In another alternate embodiment, the pump 48 might not be provided, such as when liquid from the reservoir 42 is moved, such as by suction by the fan 14, wicking or gravity fed dripping from the reservoir. In another alternate embodiment, the battery 50 might not be provided, such as when the deodorizing air system is powered by an electrical power supply other than a battery.

The liquid pump 48 comprises an inlet 52 which is adapted to mate with the outlet 46 of the reservoir 42. In a preferred embodiment the outlet 46 comprises a spring loaded poppet valve which opens when the outlet 46 is connected to the inlet 52 and, automatically closes and reseals the outlet 46 when the cartridge is removed. The pump 48 comprises an outlet or spray head 54. The outlet 54 extends into the chamber 44 for delivering liquid from the reservoir 42 into the chamber 44. Deodorizing liquid pumped into the chamber 44 by the liquid pump 48 can be atomized by the spray head 54. The spray head 54 is adapted to spray the liquid directly onto the front air entrance side of the first filter element. In a preferred embodiment the front air entrance side of the first filter element is circular and the spray pattern of the spray head 54 is circular such that the spray head 54 can spray the liquid across substantially the entire area of the air entrance side. The motion of the air flow into the air entrance side helps to push the liquid into the first filter element where it is retained. The first filter element can function as a support for supporting the liquid across the entire cross-sectional area of the air flow path. Thus, substantially all the air passing through the first filter element comes into contact with the liquid as the air passes through the first filter element. With time, evaporation and drying will occur. In alternative embodiments any suitable delivery system could be provided for depositing the liquid onto the filter element.

Referring particularly to FIG. 4, the electrical circuit 18 comprises the battery 50, the switch 20, the fan 14, the pump 48, a controller 56 and a switch 58. As noted above, the switch 20 is preferably actuated by movement of the seat S to a downward position. However, in alternate embodiments, the switch 20 might not be provided. In the embodiment shown, electrical circuit also comprises a manual override button or heavy duty button 60. The button 60 comprises a switch connected to the controller which, when manually depressed by a user, sends a signal to the controller.

In a preferred embodiment, the signal from the button 60 is sent to the controller 56 for signaling that the pump 48 should be actuated to add additional deodorizing liquid into the chamber 44 and that the fan 14 should run for a predetermined period of time even if the switch 20 is open. In an alternate embodiment, the button 60 could merely be adapted to manually close the switch 20 without the seat S being moved to its down position. In another alternate embodiment, the manual override button 60 might not be provided.

The controller 56 preferably comprises a printed circuit board with a microprocessor 62. However, in alternate embodiments, the controller 56 could comprise any suitable type of component(s). In one type of alternate embodiment, the controller 56 could comprise merely an electromechanical switch. The controller 56 is adapted to actuate the fan 14 and the liquid pump 48.

When the switch 20 is closed, electricity from the battery 50 is supplied to the controller 56. When the controller 56 is supplied with electricity, the controller 56 does not automatically actuate the fan 14 and the liquid pump 48. Instead, before actuating the fan 14 and the liquid pump 48, the controller 56 first determines if the switch 58 has been actuated. Only if the switch 58 is actuated will the controller 56 allow electricity to be supplied to the fan 14 and liquid pump 48. Thus, only if the switch 58 is actuated will the controller allow the fan 14 and liquid pump 48 to operate.

The switch 58, in the embodiment shown, comprises a reed switch. The reed switch 58 is located adjacent a receiving area for receiving the cartridge 16. More specifically, the reed switch 58 is located directly opposite the switch actuator 36 when the cartridge 16 has been properly inserted into its receiving area in the housing 12. In a preferred embodiment, the reed switch 58 is located on the printed circuit board of the controller 56. However, in alternative embodiments the reed switch 58 could be located at any suitable position. The reed switch 58 is normally maintained in an open position, but is adapted to be moved to a closed position by a magnetic field from the permanent magnet of the switch actuator 36. The reed switch 58 is adapted to be actuated or moved to a closed position by the permanent magnet of the switch actuator 36 when the switch actuator 36 is located directly opposite the reed switch. If the permanent magnet of the switch actuator 36 is not located directly opposite the reed switch 58, then the reed switch 58 remains in its deactuated or open position.

The interlock system of the embodiment shown uses a small magnet which is attached at a predetermined location on the cartridge frame. When the cartridge is properly inserted into the device, the magnet moves in close proximity to the reed switch located off the controller printed circuit board. When the reed switch closes, it triggers a relay on the controller 56 which allows operation of the unit.

The controller 56 is adapted to sense whether the reed switch 58 is in its open position or its closed position. If the reed switch 58 is in its open position, the controller 56 will not cause the fan 14 and the pump 48 to operate. However, if the reed switch 58 is in its closed position, this signals that the cartridge 16 is located in the housing 12 and orientated in a proper position, and the controller 56 can cause the fan 14 and pump 48 to operate. The system 10 preferably requires both the switches 20, 58 to be closed before the system will operate. When both switches 20, 58 are closed, the fan 14 moves air from the bowl T, through the inlet 26, and into the chamber 44. The pump 48 delivers deodorizing liquid from the reservoir 42 into the chamber 44. The atomized liquid is caught by the filter and held by the filter as a distributed support for the air to contact the liquid. The air in the chamber 44 continues to flow through the flow path, through the filter element 34, and out the outlets 40, 28.

The present invention can prevent operation if the proper filter is not being used and can also prevent operation if the filter is not in place or not orientated correctly. The present invention can use an interlock system which uses a small magnet that is attached at a predetermined location on the filter frame. When the filter is properly inserted into the device, the magnet can move in close proximity to a reed switch located off the control printed circuit board. When the reed switch closes, it can trigger a relay on the printed circuit board which allows operation of the unit. Use of the magnet and a reed switch configuration prevents the apparatus from being prone to problems relating to moisture or air contamination.

In a preferred embodiment, the controller 56 comprises a counter to count the number of times that the pump 48 is actuated to spray the liquid. The controller 56 and the pump 48 are adapted to spray a predetermined amount of liquid each time the pump is actuated. The controller 56 is preferably adapted to predict when the reservoir 42 is nearing empty based upon the number of times that the pump 48 has been actuated. The system also preferably comprises a signaling device, such as a piezo buzzer for example. The signaling device is attached to the controller 56. When the controller 56 predicts that the reservoir is about to become empty, the controller can activate the signaling device to indicate to the user that the cartridge 16 should be replaced. However, in an alternate embodiment the low reservoir signaling system might not be provided, or any suitable low reservoir or empty reservoir signaling system could be provided.

The system could also have a low voltage sensor (not shown) connected to the controller 56. When the low voltage sensor senses that the battery voltage is getting low, the controller could activate the signaling device, perhaps with a different signaling pattern from the low reservoir situation, or could activate a second signaling device (not shown). The user would then know to recharge or replace the battery 50. However, in an alternate embodiment the low voltage signaling system might not be provided, or any suitable low voltage signaling system could be provided.

Figure 5:
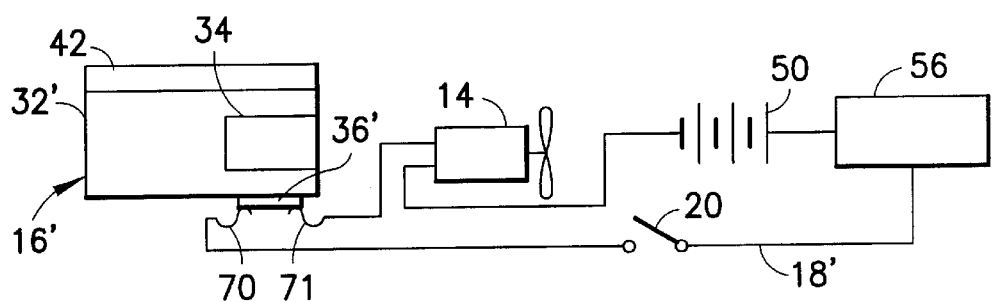
FIG. 5 is a schematic circuit diagram of an alternate embodiment of the present invention.

Referring now also to FIG. 5, an alternate embodiment of the deodorizing air system will be described. In this embodiment, the deodorizing air system generally comprises a fan 14, a removable cartridge 16', an electrical circuit 18', a power supply 50, and a controller 56. The electrical circuit 18' comprises the switch 20 and two electrical contacts 70, 71. The cartridge 16' generally comprises a frame 32', a filter element 34, and a switch actuator 36'. The cartridge 16' is adapted to be removably connected to the outlet 30 from the fan 14 inside the housing 12. The frame 32' generally comprises an air inlet, an air outlet, a liquid reservoir, and a chamber. The air inlet is removably connected to the outlet 30. The liquid reservoir 42 is adapted to hold a supply of deodorizing liquid therein.

The switch actuator 36', in the embodiment shown, comprises an electrical conductor attached to the exterior side of the frame 32'. In a preferred embodiment, the switch actuator 36' comprises a small piece of adhesive backed conductive tape. In an alternate embodiment, the switch actuator 36' could comprise a conductive stamped metal strip which is riveted, screwed or otherwise fastened into position onto the filter frame 32'. The adhesive tape is applied to a predetermined location on the filter frame.

The two contacts 70, 71 form an open circuit to the fan 14. When the cartridge 16' is properly located inside the housing, the switch actuator 36' makes electrical contact with the two contacts 70, 71. Thus, when the cartridge 16' is properly located inside the housing, the switch actuator 36' can close the open circuit between the two contacts 70, 71. When the cartridge is properly inserted into the device, the conductive tape bridges the gap between the two low voltage electrical contacts. The completed closed circuit can either be used to trigger a relay on the controller 56 or, if the current is low enough, directly power the blower motor. When the switch actuator 36' closes the open path between the contacts 70, 71, the controller 56 can actuate the fan 14 when the switch 20 is closed.

If the cartridge 16' is not properly located inside the housing, the open circuit between the two contacts 70, 71 prevents the fan 14 from operating. Therefore, only when the cartridge 16' is properly located in the housing of the deodorizing air system is the fan 14 allowed to operate. If the cartridge 16 is improperly located in the deodorizing air system housing, or no cartridge is located inside the housing, then the deodorizing air system will not function. This prevents the fan 14 from moving air out of the bowl T without the cartridge 16' being properly operationally inserted in the deodorizing air system housing, thus, preventing the deodorizing air system from moving unfiltered air out of its housing. In alternate embodiments, any suitable type of the interlock or signaling system for preventing the deodorizing air system from operating unless the combined air filter and liquid deodorizer cartridge is properly inserted could be provided. Features of the present invention can be applied to other products, such as a room air purifier.

Figure 6:
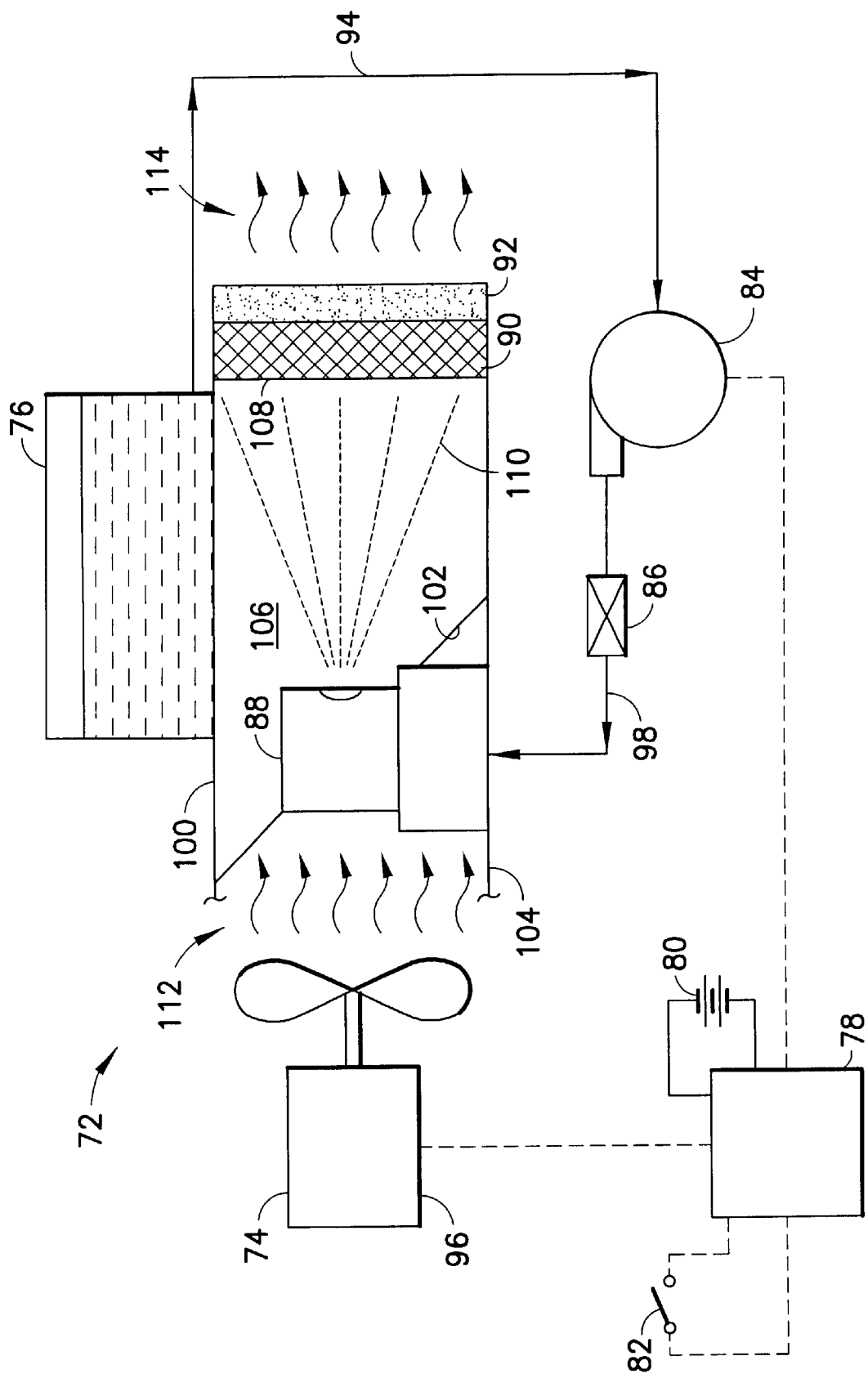
FIG. 6 is a diagram of another embodiment of the present invention.

Referring also to FIG. 6, there is shown a diagram of an alternate embodiment of the present invention. In this embodiment the system 72 generally comprises an air blower system 74, a fluid reservoir 76, a controller 78, a battery 80, a user presence switch 82, a liquid pump 84, a check valve 86, a spray head 88, and a filter comprising a first filter element 90 and a second filter element 92. The controller 78 controls the operation of the fluid pump 84 and the motor 96 of the air blower system 74. The fluid reservoir 76 comprises an odor neutralizing solution therein. The fluid reservoir 76 is connected to the liquid pump 84 by a fluid conduit 94. An outlet of the fluid pump 84 is connected to the spray head 88 through the check valve 86 and a fluid conduit 98. The filter elements 90, 92 and the fluid reservoir 76 are provided as a cartridge.

A frame 100 of the cartridge has an open angled side 102 which mates with a portion of the housing 104 to form an air flow duct 106 from the air blower system 74. The spray head 88 is fixedly attached to the housing 104 and is located in the duct 106. The frame 100 can be positioned over the spray head 88. The spray head 88 comprises a suitable spray pattern and is suitably spaced from the front side 108 of the first filter element 90 such that the spray pattern 110 of fluid from the spray head 88 substantially covers the entire area of the front side 108.

The foul air drawn in from the toilet, as illustrated by arrows 112, is pushed by the air blower system 74 through the air flow duct 106 and into the filter element 90, 92. The spray head 88 is adapted to spray the odor neutralizing solution onto the front side 108 of the first filter element 90. Thus, air passing through the first filter element 90 will make contact with the odor neutralizing solution located on the first filter element 90. The cleaned air then exits from the cartridge as illustrated by arrows 114.

One of the features of the present invention is in regard to the improved odor removal function from the combined use of a deodorizing liquid and the filter arrangement. It has been discovered that certain deodorizing liquids work very well in this combination to remove airborne odors and not merely mask them. In particular, tests were conducted using commercially available deodorizing liquids; namely, FEBREZE™,(unscented, and three scented: A, B and C), ODOBAN™, and ZEOCRYSTAL FRESH AIR MIST™.

FEBREZE™ is manufactured and distributed by The Procter & Gamble Company of Cincinnati, Ohio. It is described in U.S. Pat. Nos. 5,942,217, 5,939,060, 5,783,544, 5,714,137, 5,668,097 and 5,593,670 which are hereby incorporated by reference in their entireties. "FEBREZE™ A", "FEBREZE™ B" and "FEBREZE™ C" were samples of FEBREZE™ supplied by The Procter & Gamble Company under those trade names, all having the same active ingredients, but merely having different scent perfume additives. FEBREZE™ comprises uncomplexed cyclodextrin in an aqueous solution. More specifically, FEBREZE™ generally comprises an aqueous odor-absorbing composition, preferably for use on inanimate surfaces.

ODOBAN™ is manufactured and distributed by Clean Central Corp. of Warner Robins, Ga. Its active ingredient is alkyl ($C_{14}$ 50%, $C_{12}$ 40% and $C_{16}$ 10%) dimethyl benzyl ammonium chloride which is an antibacterial quaternary ammonium compound. The alkyl dimethyl benzyl ammonium chloride is in a solution with water and isopropanol. Another product by Clean Control Corp. is BIOODOR CONTROL™ which includes water, bacterial spores, alkylphenol ethoxylate and propylene glycol.

ZEOCRYSTAL FRESH AIR MIST™ is manufactured and distributed by Zeo Crystal Corp. (a/k/a American Zeolite Corporation) of Crestwood, Ill. The liquid comprises chlorites, oxygen, sodium, carbonates and citrus extract, and may comprise zeolite.

These products all either "trap", "absorb" or "destroy" odor molecules to thereby separate or remove odor from air. These types of solutions are referred to herein as an "odor eliminator liquid". The odor eliminator liquid has the property of being able to trap, absorb or destroy an odor molecule; rather than merely masking the odor such as with a perfume. Another odor eliminator liquid might include alcohol.

The tests were performed with the above-noted odor eliminator liquids and with specific types of second filter elements which included an activated carbon pad 0.187 inch thick, a filter element impregnated with baking soda, and a filter element impregnated with zeolite mineral. In alternative embodiments, other types of second filter elements could be provided. Three or more different filter elements could also be provided. The test procedure comprised:

1. Place dog fecal sample in toilette bowl and secure top cover in place.
2. Spray primary filter with odor eliminator liquid using fixture setup.
3. Immediately place primary and secondary filters in prototype exhaust tube and turn on the blower motor.
4. Each test subject (Judge) smelt the exhaust air and rated the objectionability of the odor on a scale of 1 to 5. A value of 1 is low objection and a 5 is high.
5. Between test subjects the blower motor was shut off to avoid complete evaporation of the solution.

The following four tables show the results using different judges (A–Q). Each judge gave the odor, after exiting the test apparatus, a number ranking of 1–5. The best results were obtained in test 22 which used ODOBAN™ sprayed onto the first filter and a second filter element which comprised a filter impregnated with zeolite mineral.

Test Results: (Phase 1)

| Test No. | Solution Type | Secondary Filter Type | Number Ranking Judge A | Number Ranking Judge B | Number Ranking Judge C | Number Ranking Judge D | Number Ranking Judge E | Average Ranking |
|---|---|---|---|---|---|---|---|---|
| 1 | None (Baseline) | None | 5 | 5 | 5 | 5 | 5 | 5.0 |
| 2 | Febreze A | Carbon A 0.187" tk | 4 | 5 | 4 | 4 | 3 | 4.0 |

-continued

Test Results: (Phase 1)

| Test No. | Solution Type | Secondary Filter Type | Number Ranking Judge A | Number Ranking Judge B | Number Ranking Judge C | Number Ranking Judge D | Number Ranking Judge E | Average Ranking |
|---|---|---|---|---|---|---|---|---|
| 3 | Febreze C | Carbon A 0.187" tk | 1 | 4 | 2 | 4 | 4 | 3.0 |
| 4 | Febreze C | Carbon A 0.187" tk | 3 | 4 | 1 | 5 | 4 | 3.4 |
| 5 | Febreze Unscented | Carbon A 0.187" tk | 5 | 5 | 3 | 5 | 5 | 4.6 |
| 6 | ZeoCrystal Fresh Air Mist | Carbon A 0.187" tk | 2 | 1 | 1 | 2 | 2 | 1.6 |
| 7 | Febreze A | Baking Soda | 5 | 4 | 4 | 3 | 2 | 3.6 |
| 8 | Febreze B | Baking Soda | 4 | 3 | 4 | 3 | 3 | 3.4 |
| 9 | Febreze C | Baking Soda | 3 | 3 | 2 | 2 | 3 | 2.6 |
| 10 | Febreze Unscented | Baking Soda | 3 | 3 | 2 | 3 | 3 | 2.8 |
| 11 | ZeoCrystal Fresh Air Mist | Baking Soda | 4 | 2 | 2 | 2 | 1 | 2.2 |

Test Results: (Phase 2)

| Test No. | Solution Type | Secondary Filter Type | Number Ranking Judge A | Number Ranking Judge F | Number Ranking Judge C | Number Ranking Judge G | Number Ranking Judge E | Number Ranking Judge H | Average Ranking |
|---|---|---|---|---|---|---|---|---|---|
| 12 | None (Baseline) | None | 5 | 5 | 5 | 5 | 5 | 5 | 5.0 |
| 13 | ZeoCrystal Fresh Air Mist | Carbon A 0.187" tk | 3 | 4 | 3 | 3 | 3 | 4 | 3.3 |
| 14 | Febreze C | Baking Soda | 3 | 2 | 1 | 3 | 2 | 3 | 2.3 |

Test Results: (Phase 3)

| Test No. | Solution Type | Secondary Filter Type | Number Ranking Judge I | Number Ranking Judge J | Number Ranking Judge D | Number Ranking Judge K | Number Ranking Judge L | Number Ranking Judge M |
|---|---|---|---|---|---|---|---|---|
| 15 | None (Baseline) | None | 5 | 5 | 5 | 5 | 5 | 5 |
| 16 | ZeoCrystal Fresh Air Mist | Carbon A 0.187" tk | 4 | 4 | 3 | 2 | 3 | 4 |
| 17 | Febreze C | Baking Soda | 3 | 4 | 2 | 3 | 4 | 4 |
| 18 | Odoban | Baking Soda | 2 | 3 | 1 | 2 | 2 | 3 |

| Test No. | Solution Type | Secondary Filter Type | Number Ranking Judge N | Number Ranking Judge O | Number Ranking Judge F | Average Ranking |
|---|---|---|---|---|---|---|
| 15 | None (Baseline) | None | 5 | 5 | 5 | 5 |
| 16 | Zeocrystal Fresh Air Mist | Carbon A 0 187" tk | 3 | 3 | 2 | 3.1 |
| 17 | Febreze C | Baking Soda | 1 | 2 | 3 | 2.9 |
| 18 | Odoban | Baking Soda | 2 | 4 | 2 | 2.3 |

Test Results: (Phase 4)

| Test No. | Solution Type | Secondary Filter Type | Number Ranking Judge C | Number Ranking Judge P | Number Ranking Judge D | Number Ranking Judge H | Number Ranking Judge Q | Number Ranking Judge L | Average Ranking |
|---|---|---|---|---|---|---|---|---|---|
| 19 | None (Baseline) | None | 5 | 5 | 5 | 5 | 5 | 5 | 5.0 |
| 20 | ZeoCrystal Fresh Air Mist | Zeolite | 2 | 2 | 1 | 4 | 3 | 2 | 2.3 |
| 21 | Febreze C | Zeolite | 3 | 2 | 3 | 4 | 4 | 2 | 3.0 |
| 22 | Odoban | Zeolite | 1 | 1 | 2 | 2 | 2 | 1 | 1.5 |

The present invention can be used by passing foul odors through an open fiber polyester filter media that has been sprayed with an odor eliminator liquid such as FEBREZE™, ODOBAN™ or ZEOCRYSTAL FRESH AIR MIST™. For added protection, a secondary filter, such as activated carbon, zeolite, or polyester impregnated with baking soda, can be used to further assist in neutralizing odors. Foul air odors can be drawn directly from the toilet bowl by a fan blower arrangement and directly into an enclosure positioned directly behind the toilet seat. The closure can house a cone-shaped removable cartridge assembly consisting of a fluid reservoir, air duct, and a multi-filter arrangement. In addition, the closure can also contain an electric powered pump spray system, a centrifugal fan, an inlet filter, and an electronic controller. All electrical systems can be powered with a rechargeable nickel cadmium (NiCad) battery which is easily removed for recharging.

The spray head for delivering the odor eliminator liquid is preferably fixed to the bottom of the mating closure. When the removable cartridge is inserted in place, the spray head gets positioned between the outlet of the blower and the filters. When activated, the liquid can get dispersed evenly on the first filter. The dispersion is further assisted by the air stream moving past the spray head which helps to move the solution towards the filter.

In operation, the system can work as follows:

The user sits down on the toilet seat causing the rear support to move inside the enclosure. This action activates a switch located on the controller which turns ON the blower. At the same time the spray pump its activated for approximately 150 milliseconds.

Odor eliminator liquid is drawn from the reservoir and sprayed on the first filter in a metered amount of approximately 0.25 ml.

Air is drawn through the first filter, which has been saturated with solution, and then passes through the second odor absorbent filter before exiting the main housing.

The air blower continues to operate as long as the user remains seated. When the user gets up, the blower will continue for a short duration before it automatically turns off. If the user remains seated for an extended time duration (i.e. 3 minutes) the blower can shut off to prevent the batteries from draining.

If the user requires additional odor protection while seated, a heavy duty button is provided which activates the sprayer an additional 150 milliseconds each time it is pressed.

When the unit is used for the very first time, it might be necessary to prime the pump system. This can be accomplished by keeping the heavy duty button depressed for five seconds which signals the electronics to operate the pump for several seconds until priming occurs.

In alternative methods, any suitable time periods and quantities of solution could be used.

Referring now to FIGS. 7 and 8, one embodiment of an air deodorizer cartridge 120 incorporating features of the present invention is shown. The cartridge 120 generally comprises a frame 122 and a filter 124. The frame 122 generally comprises a first section 126 and a second section 128. However, in alternate embodiments, the frame 122 could comprise more or less than two sections. The first section 126 forms an air flow channel 130 and an air filter holding area 132.

An inlet or entrance 134 into the air flow channel 130 is sized and shaped to form a receiving area 136 for receiving a portion of a liquid spray head. The inlet 134 is also sized and shaped to mate with a mating air flow channel in the air deodorizing apparatus (not shown) which the cartridge 120 is intended to be removably connected to. The bottom 138 of the frame 120 is adapted to mount the frame 120 to the frame of the air deodorizing apparatus.

The filter 124 preferably comprises a multistage filter comprising at least two different types of filter elements, such as the filter elements described above. However, in alternate embodiments, any suitable type of filter could be used. The filter 124 is stationarily received in the air filter holding area 132.

The second section 128 of the frame 122 forms a liquid reservoir 140. The second section 128 comprises an outlet 142 from the liquid reservoir 140. In the embodiment shown, the liquid outlet 142 faces in a downward direction. However, in alternate embodiments, the liquid outlet could face any suitable direction. The cartridge 120 is preferably supplied with a supply of odor eliminator liquid inside the liquid reservoir 140. The cartridge 120 preferably comprises a seal 144 located in the outlet 142. In a preferred embodiment the seal 144 comprises a spring loaded poppet valve which opens when the outlet 142 is connected to the inlet to the pump and, automatically closes and reseals the outlet 142 when the cartridge is removed.

In an alternate embodiment, the seal 144 could comprise a membrane which prevents the odor eliminator liquid inside the liquid reservoir 140 from spilling out of the reservoir unless the cartridge is attached to the air deodorizing apparatus. When the cartridge 120 is attached to the air deodorizing apparatus, the membrane can be automatically pierced to allow liquid in the reservoir 140 to pass out of the outlet 142. In alternate embodiments, any suitable type of system for sealing the outlet 142 until connected to the deodorizing apparatus could be provided.

The liquid reservoir 140 of the cartridge 120 is generally intended not to be refillable. Instead, when the liquid reservoir 140 is depleted, it is intended for the cartridge 120 to be replaced with a new cartridge. However, in alternate embodiments, the second section 128 could be constructed such that the liquid reservoir could be refilled. When the cartridge 120 is attached to the liquid pump of the air deodorizing apparatus, a spray head of the pump can spray the odor eliminator liquid onto the first filter element of the filter 124.

The second section 128 preferably comprises a vent hole 184 in its top side 186. The vent hole 184 allows the liquid to flow out of the reservoir 140 without a vacuum being created in the reservoir and thereby interfering with the flow of the liquid out of the reservoir. In a preferred embodiment, the vent hole 184 is initially covered by a movable member, such as tape. The user can remove the tape when the cartridge is installed into the system. However, in alternate embodiments, any suitable system for preventing a vacuum from hindering the flow of liquid out of the reservoir could be provided.

In the embodiment shown, the first and second sections 126, 128 are fixedly and stationarily connected to each other. In a preferred embodiment, the frame 122 is comprised of molded plastic and the first and second sections 126, 128 are separately formed and subsequently fixedly and stationarily connected to each other to form a unitary structure. However, in alternate embodiments, the first and second sections 126, 128 could be integrally molded with each other. In the embodiment shown, the air deodorizer cartridge 120 does not comprise a switch actuator, such as the magnet 36 or contact 36' described with reference to FIGS. 4 and 5. However, in alternate embodiments, a switch actuator (such as the magnet 36) could be provided.

In the embodiment shown, the cartridge 120 further comprises a sponge 139 connected to the frame 122 inside the air flow channel 130. However, in an alternate embodiment, the sponge might not be provided. The sponge is located in a pocket 182 in the bottom 138 of the frame 122. The pocket 182 has a general rectangular shape and the sponge 139 also has a general rectangular shape. However, in alternate embodiments, any suitable shapes could be provided. The sponge 139 is provided to absorb an excess liquid which, because of gravity, flows down to the bottom of the inside of the cartridge. The excess liquid could comprise liquid that contacts the sides of the air flow channel 130 or liquid in mist form that does not reach the first air filter element, or which runs down the front face of the first air filter element. Over time, the liquid which is not collected by the sponge 139 could puddle in the bottom of the air flow channel and spill out when the user replaces the cartridge. In an alternate embodiment, any suitable type of puddle preventing system could be provided.

Figure 9:
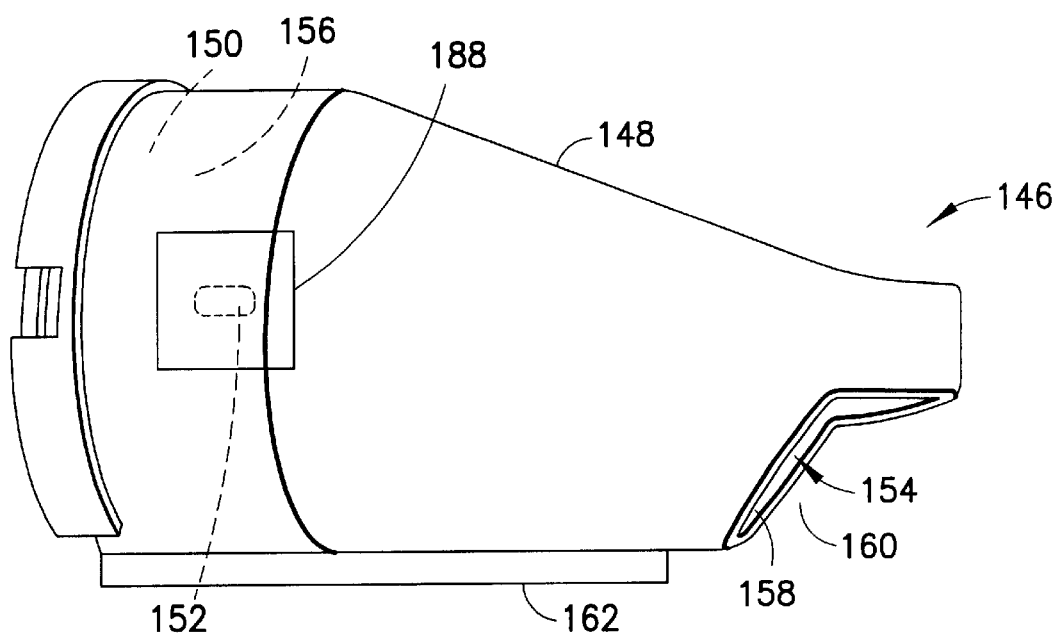
FIG. 9 is a side perspective view of another embodiment of the air deodorizer cartridge incorporating features of the present invention.

Referring now to FIG. 9, an alternate embodiment of the air deodorizer cartridge 146 is shown. In this embodiment the air deodorizer cartridge 146 does not comprise a liquid reservoir. The air deodorizer cartridge 146 generally comprises a frame 148, a filter 150, and a switch actuator 152. The frame 148 forms an air flow channel 154 and an air filter holding area 156. The frame 148 is substantially identical to the first section 126 of the frame 122 shown in FIGS. 7 and 8.

An inlet or entrance 158 into the air flow channel 154 is sized and shaped to form a receiving area 160 for receiving a portion of a liquid spray head. The inlet 158 is also sized and shaped to mate with a mating air flow channel in the air deodorizing apparatus (see FIG. 10) which the cartridge 146 is intended to be removably connected to. The bottom 162 of the frame 148 is adapted to mount the frame 148 to the frame of the air deodorizing apparatus.

The filter 150 preferably comprises a multistage filter comprising at least two different types of filter elements, such as the filter elements described above. However, in alternate embodiments, any suitable type of filter could be used. The filter 150 is stationarily received in the air filter holding area 156. The switch actuator 152 preferably comprises a permanent magnet. However, in an alternate embodiment, the switch actuator could comprise any suitable type of switch actuator, such as an electrical contact. The switch actuator 152 is fixedly and stationarily connected to the lateral side of the frame 148. However, in alternate embodiments, the switch actuator 152 could be mounted to any suitable location on the frame 148.

In a preferred embodiment, the air deodorizing apparatus comprises a printed circuit board which is located on the lateral side of the cartridge 146. The printed circuit board comprises a reed switch which is adapted to be actuated by the magnet 152 when the cartridge 146 is inserted into a proper position in the air deodorizing apparatus.

In a preferred embodiment, the frame 148 has a pocket which receives the magnet 152 and a piece of tape 188 is located on the frame and over the magnet to prevent the magnet from falling out of the pocket. The tape can seal off the magnet from the surrounding atmosphere. Some magnets might rust when exposed to moisture. Moisture exists near a toilet, and could be present during shipping or storage of the cartridge before installation into the system. Thus, the tape can both keep the magnet attached to the frame and, prevent the magnet from rusting and potentially not opening the reed switch. However, in alternate embodiments, any suitable type of system for attaching the magnet to the frame and/or preventing the magnet from being exposed to ambient moisture could be provided.

Figure 10:
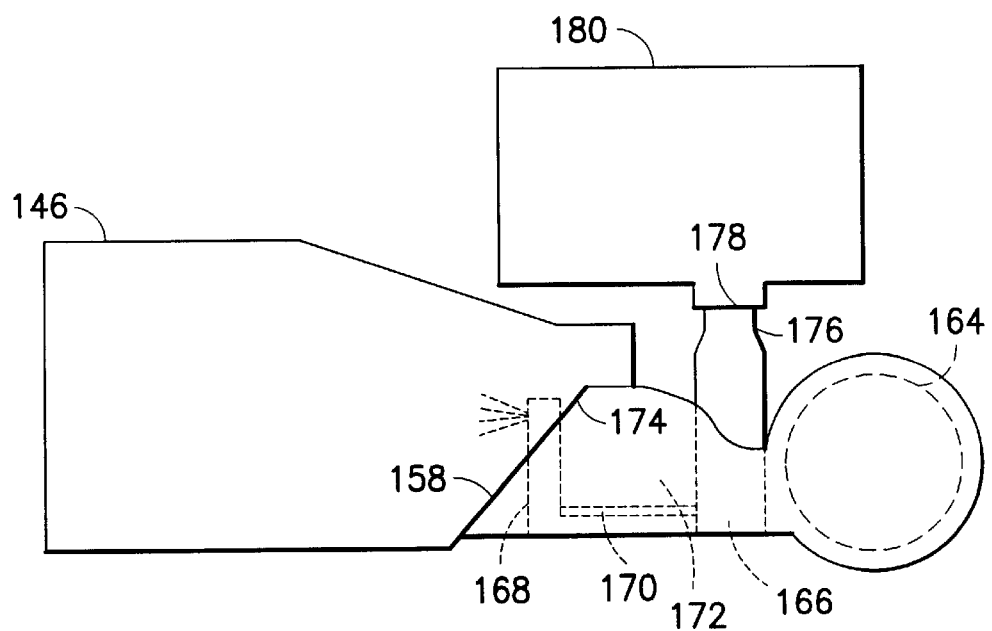
FIG. 10 is a block diagram of portions of an alternate air deodorizing apparatus using the air deodorizer cartridge shown in FIG. 9.

Referring also to FIG. 10, a block diagram showing the cartridge 146 connected to some of the components of an air deodorizing apparatus is shown. The air deodorizing apparatus includes an air driver 164, and a liquid pump 166 connected to a liquid spray head 168 by a tube 170. A portion 172 of the housing of the air deodorizing apparatus forms an air flow channel from the air driver 164 to the cartridge 146. The inlet 158 is adapted to mate with the outlet 174 of the portion 172 which forms the mating air flow channel. The pump 166 comprises a section 176 which is adapted to be connected to an outlet 178 of a fluid container 180. The fluid container 180 comprises a liquid reservoir for storing the odor eliminator liquid. The fluid container 180 is provided separately from the cartridge 146. This embodiment illustrates that the liquid reservoir need not be provided as an integral part of the air filter cartridge.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. An air deodorizer cartridge comprising:
  a frame including a first section and a second section, the first section forming an air flow channel and an air filter holding area, the second section forming a liquid reservoir; and
  at least one air filter element located in the filter holding area, wherein the first and second sections of the frame are fixedly coupled to each other as a unitary structure for insertion of the air deodorizer cartridge into an air deodorizing apparatus as a singular cartridge unit.

2. An air deodorizer cartridge as in claim 1 further comprising a magnet connected to the frame.

3. An air deodorizer cartridge as in claim 2 wherein the magnet is mounted to a lateral side of the frame.

4. An air deodorizer cartridge as in claim 1 wherein the at least one air filter element comprises at least two different air filter elements.

5. An air deodorizer cartridge as in claim 1 further comprising an odor eliminator liquid located in the liquid reservoir.

6. An air deodorizer cartridge as in claim 5 wherein the odor eliminator liquid is also located on the air filter element.

7. An air deodorizer cartridge as in claim 1 wherein the second section comprises a liquid outlet adapted to be connected to a liquid pump.

8. An air deodorizer cartridge as in claim 1 wherein an inlet into the air flow channel comprises a receiving area for receiving a portion of a liquid spray head.

9. An air deodorizer cartridge as in claim 1 wherein the second section comprises an air vent hole into the liquid reservoir, and the cartridge further comprises tape located on the frame over the air vent hole, wherein the tape can be removed to open the air vent hole.

10. An air deodorizer cartridge comprising:

a frame forming an air flow channel and an air filter holding area;

at least one air filter element located in the filter holding area; and a magnet connected to the frame, wherein the frame is sized and shaped to be inserted into a mating receiving area of an air deodorizing apparatus such that the air flow channel mates with a mating air flow channel in the apparatus, and wherein the magnet is positioned directly opposite a reed switch of the air deodorizing apparatus to thereby actuate the reed switch.

11. An air deodorizer cartridge as in claim 10 wherein the frame further comprises a liquid reservoir.

12. An air deodorizer cartridge as in claim 11 wherein the liquid reservoir is stationarily connected to a section of the frame forming the air flow channel.

13. An air deodorizer cartridge as in claim 11 wherein the liquid reservoir comprises a downwardly facing liquid outlet adapted to be connected to a liquid pump.

14. An air deodorizer cartridge as in claim 11 further comprising an odor eliminator liquid located in the liquid reservoir.

15. An air deodorizer cartridge as in claim 14 wherein the odor eliminator liquid is also located on the air filter element.

16. An air deodorizer cartridge as in claim 10 wherein an inlet into the air flow channel comprises a receiving area for receiving a portion of a liquid spray head.

17. An air deodorizer cartridge as in claim 10 wherein the magnet is stationarily connected to a lateral side of the frame.

18. An air deodorizer cartridge as in claim 10 wherein the at least one air filter element comprises at least two different air filter elements.

19. An air deodorizer cartridge as in claim 10 further comprising tape connected to the frame, the tape connecting the magnet to the frame and sealing off the magnet from ambient atmosphere moisture.

20. A method of manufacturing an air deodorizer cartridge comprising steps of:

forming a unitary frame with a first section having an air flow channel and a second section having a liquid reservoir;

inserting an air filter element into the first section of the frame; and inserting deodorizing liquid into the liquid reservoir of the second section.

21. A method as in claim 20 further comprising connecting a magnet to the frame.

22. A method as in claim 20 wherein the step of inserting the air filter element into the first section comprises inserting at least two different air filter elements into the first section.

* * * * *